United States Patent [19]

Mullins

[11] Patent Number: 5,266,800
[45] Date of Patent: Nov. 30, 1993

[54] METHOD OF DISTINGUISHING BETWEEN CRUDE OILS

[75] Inventor: Oliver C. Mullins, Ridgefield, Conn.

[73] Assignee: Schlumberger Technology Corporation, New York, N.Y.

[21] Appl. No.: 955,100

[22] Filed: Oct. 1, 1992

[51] Int. Cl.$^5$ .................. G01V 9/04; G01N 21/31; G01N 21/35
[52] U.S. Cl. .................. 250/256; 250/253; 250/301; 250/343; 250/339; 250/255; 356/70
[58] Field of Search .................. 356/70; 250/301, 253, 250/255, 256, 343, 339

[56] References Cited

U.S. PATENT DOCUMENTS

| | | | |
|---|---|---|---|
| 2,334,475 | 11/1943 | Claudet | 250/71 |
| 2,423,774 | 7/1947 | Heigl | 250/83 |
| 2,425,531 | 8/1947 | Haseltine et al. | 88/14 |
| 3,371,574 | 4/1968 | Dwyer | 88/14 |
| 3,859,851 | 1/1975 | Urbanosky | 73/155 |
| 3,896,312 | 7/1975 | Brown et al. | 250/343 |
| 4,227,083 | 10/1980 | Sherinski | 250/343 |
| 4,371,785 | 2/1983 | Pedersen | 250/343 |
| 4,396,259 | 8/1983 | Miller | 351/158 |
| 4,427,944 | 1/1984 | Chandler | 324/353 |
| 4,492,862 | 1/1985 | Grynberg et al. | 250/255 |
| 4,540,283 | 9/1985 | Bachalo | 356/336 |
| 4,602,160 | 7/1986 | Mactaggart | 250/341 |
| 4,608,859 | 9/1986 | Rockley | 73/153 |
| 4,609,821 | 9/1986 | Summers | 250/255 |
| 4,620,284 | 10/1986 | Schnell et al. | 364/498 |
| 4,663,961 | 5/1987 | Nelson et al. | 73/24 |
| 4,994,671 | 2/1991 | Safinya et al. | 250/255 |
| 5,166,747 | 11/1992 | Schroeder et al. | 250/256 |

OTHER PUBLICATIONS

Flow Vision on Line Infrared Analyzers, trade brochure, Flow Vision, Inc., Clifton, N.J., undated.
Plastic Compounding article—vol. 10, No. 5 Jul./Aug. 1987 "Spotlight: Online Image Analyzer Monitors Melt Stream . . . ".
1986 Polymers, Lamination and Coatings Conf.-Book 2 Oct. 1986, Kilham et al., "On-Line Particulate Analysis of Polymers and Compound: In-the-Melt Vs. Finished Product Studies", pp. 355–361.
Flow Vision Continuous on Line Analyzer, trade brochure, Flow Vision, Inc., Clifton, N.J., undated.
Flow Vision-The Dawn of a New Age in On Line Quality Control, trade brochure, Flow Vision, Inc., Clifton, N.J., undated.
Flow Vision Analyzer-On-Line real time display with counting and size distribution analysis . . . , trade brochure, Flow Vision, Inc., Clifton, N.J., undated.
The Flow Vision Analyzer-On Line Research Particle Analysis, trade brochure, Flow Vision Inc., Clifton, N.J., undated.

*Primary Examiner*—Carolyn E. Fields
*Attorney, Agent, or Firm*—David P. Gordon; Leonard W. Pojunas

[57] ABSTRACT

Methods for distinguishing among oil samples, and more particularly between a fluid containing oil base mud and formation oil samples are described. The methods all rely on the discovery that the optical absorption spectrum of all crude oils in the visible and near infrared spectra can be described according to the equation $OD = ae^{Eb}$, where (OD) is a measured optical density, (b) is a value between 0.37 and 0.55 chosen according to the wavenumber (E) and can be chosen as a constant equal to $4.6 \times 10^{-4}$ cm, and (a) is an unknown which classifies the crude oil. By making measurements and solving for (a), a crude oil can be classified. In a flow stream which has a changing oil content, such as may be obtained by a borehole tool which obtains fluid samples from the formation, by monitoring the unknown (a), a determination may be made as to when a formation oil is being obtained as opposed to a mud filtrate.

20 Claims, 8 Drawing Sheets

METHOD OF DISTINGUISHING BETWEEN CRUDE OILS

BACKGROUND OF THE INVENTION

This invention relates to methods for classifying crude oils and distinguishing among crude oils by reference to the absorption spectra of the crude oils. This invention further and more particularly relates to methods of distinguishing between oil based mud filtrates and formation oil samples which are obtained by a fluid sampling borehole tool.

As seen in FIG. 1, several different interactions may occur when light strikes a sample. Typically, if the sample is fluid, some light is reflected at the boundary of the sample while the rest of the light enters the sample. Inside the sample, light is scattered by molecular excitations (Raman scattering) and by collective modes of the medium (e.g., Rayleigh scattering). In general, only a very small fraction of the light is scattered per centimeter of path by the Raman and Rayleigh scattering processes. Rather, depending upon the sample, much of the light is often absorbed. The absorption mechanisms of interest for the present invention include the electronic absorption which relates to the excitation of electronic transitions in aromatic molecules in the fluid such as asphaltenes, resins, and porphyrins; not the vibrational absorption which results from the excitation of overtones of molecular vibrations involving hydrogen atoms.

Because different fluid samples absorb energy differently, the fraction of incident light absorbed per unit of pathlength in the sample depends on the composition of the sample and the wavelength of the light. Thus, the amount of absorption as a function of the wavelength of the light, hereinafter referred to as the "absorption spectrum", has been used in the past as an indicator of the composition of the sample. For example, in U.S. Pat. No. 4,994,671 to Safinya et al., assigned to the assignee hereof, and hereby incorporated by reference herein in its entirety, it is taught, among other things, that the absorption spectrum in the wavelength range of 0.3 to 2.5 microns can be used to analyze the composition of a fluid containing oil. The disclosed technique fits a plurality of data base spectra related to a plurality of oils and to water, etc., to the obtained absorption spectrum in order to determine the amounts of different oils and water that are present in the sample.

Numerous other techniques utilizing different parts of the spectrum are known in the arts for identifying or distinguishing between oils. For example, in U.S. Pat. No. 4,620,284 to Schnell, a helium-neon laser is used to provide photons of a 0.633 micron wave length which are directed at a sample. The resulting Raman spectrum which comprises scattered light at different wavelengths than the incident light is measured, and the measured spectrum is compared with previously obtained reference spectra of a plurality of substances in order to monitor fluid flowing through an oil refinery pipeline.

In U.S. Pat. No. 4,609,821 to Summers, especially prepared rock cuttings containing at least oil from an oil-based mud are excited with ultraviolet radiation with a 0.26 micron wave length, and the frequency and intensity of the resulting excited waves (fluorescence) which are at a longer wavelength than the incident radiation are detected and measured. By comparing the fluorescent spectral profile of the detected waves with similar profiles of the oil used in the oil-based mud, a determination is made as to whether the formation oil is also found in the rock cuttings.

In U.S. Pat. No. 3,896,312 to Brown et al., which is directed specifically to finding the source of a fuel oil leak or spill, crude oil samples are obtained and are prepared in a manner such that they are of the order of 0.1 mm thick. The crude oil samples are then analyzed to find "fingerprint" valleys in the infrared spectra in the 600–1200 cm$^{-1}$ (8.3 to 16.6 micron wavelength) range, and are compared against a library of reference samples so as to identify which specific oil has been found among the different types of fuel oils.

While the Schnell, Summers, and Brown et al. techniques, and many other similar techniques of the prior art may be useful in certain very limited areas, it will be appreciated that they suffer from various drawbacks. For example, the use of laser equipment in Schnell severely restricts the environment in which the apparatus may be used, as lasers are not typically suited to harsh temperature and/or pressure situations such as a borehole environment. Also, the use of the Raman spectrum in Schnell imposes the requirement of equipment which can detect with very high resolution the low intensity scattered signals. The use by Summers of light having a 0.26 micron wavelength, and in Brown et al., of light in the 8.3 to 16.6 micron wavelength, severely limits the investigation of the samples to samples having nominal thickness. In fact, the Summers patent requires that the sample be diluted with solvents before investigation, while the Brown et al. patent requires that the sample be prepared to a thickness of 0.1 mm. Thus, the Summers and Brown et al. patents, do not permit an analysis of formation fluids in situ. On the other hand, while the Safinya et al. disclosure is much less limited, and has been found to be generally useful in analyzing the composition of a formation fluid either in situ or at the surface, it will be appreciated that the interpretation techniques disclosed therein are commmputationally intensive. Particularly, large computing power is necessary to take a data base of spectra of numerous oils and water, and to fit those spectra to an obtained spectra in order to determine the compositional make-up of the sample. In downhole (in situ) situations, however, where the monitoring of a changing fluid flowstream in real time is desirable, and where it is less important to determine exactly the type of oil which is being obtained from the formation than it is to determine when the formation oil is being obtained as opposed to mud filtrate, it is advantageous to use less computationally intensive techniques.

SUMMARY OF THE INVENTION

It is therefore an object of the invention to provide computationally simple methods for distinguishing between a fluid containing borehole mud filtrate and formation oil.

It is another object of the invention to provide relatively computationally simple methods for classifying oil samples so as to distinguish among different oils.

In accord with the objects of the invention, a computationally simple method for classifying an oil sample is provided and generally comprises making optical density measurements (OD) of an oil sample by detecting photons of an energy in the ultraviolet, visible, or near infrared spectrum, and using the optical density measurement results to solve an equation which relates the optical density OD to a dominant term $ae^{Eb}$ for an unknown (a) which classifies the oil, where E is a wavenumber corresponding to the photon energy, and (b) is an exponential decay constant (in terms of wavenumber) which is largely independent of the wavenumber E for the oil sample. If desired, (b) may be chosen as a constant value for all oil samples at all energies, or may be provided a value of between 0.37 and 0.55 cm chosen according to the wavenumber E based on empirical data. Preferably, photons of several different energies are used in conjunction in helping to find the unknown (a). In choosing photon energies to be detected, the area of the absorbance spectrum which is dominated by electronic absorption (e.g., 200 to 1150 nm) is utilized as opposed to spectral, areas dominated by vibrational absorption. Spectral energies where water absorption is large are also preferably avoided.

Because only a single optical density measurement at a single energy is required to define the (a) value of a crude oil (although measurements at several energies are preferred), and because it is computationally simple to solve the provided equation for the (a) value given the absorption measurements (OD), the method for classifying an oil sample can be done in real time. In fact, the method for classifying an oil sample can be done downhole in a borehole tool having a downhole processing means. Thus, the disclosed methods for classifying oil samples can be extended to methods for monitoring a flow stream downhole to distinguish between when a borehole tool is obtaining primarily formation fluids as opposed to receiving an oil based mud filtrate.

A better understanding of the invention, and additional advantages and objects of the invention will become apparent to those skilled in the art upon reference to the detailed description and the accompanying drawings.

DETAILED DESCRIPTION OF THE PREFERRED EMBODIMENT

Figure 1:
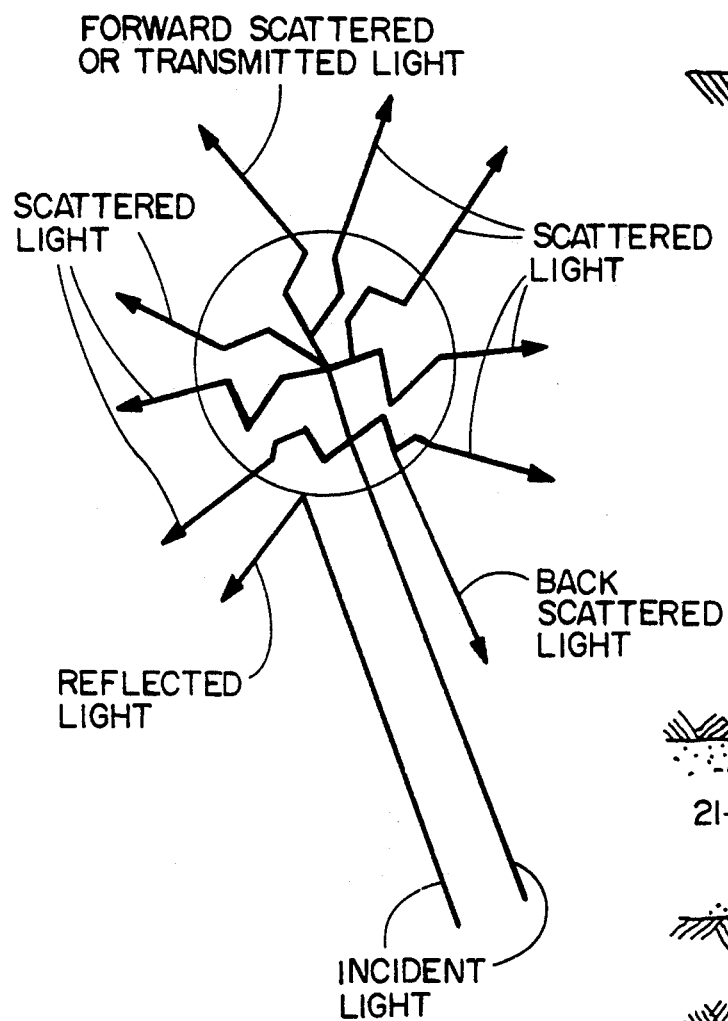
FIG. 1 is a diagram of some of the different interactions which may occur when light strikes a sample.
Figure 2:
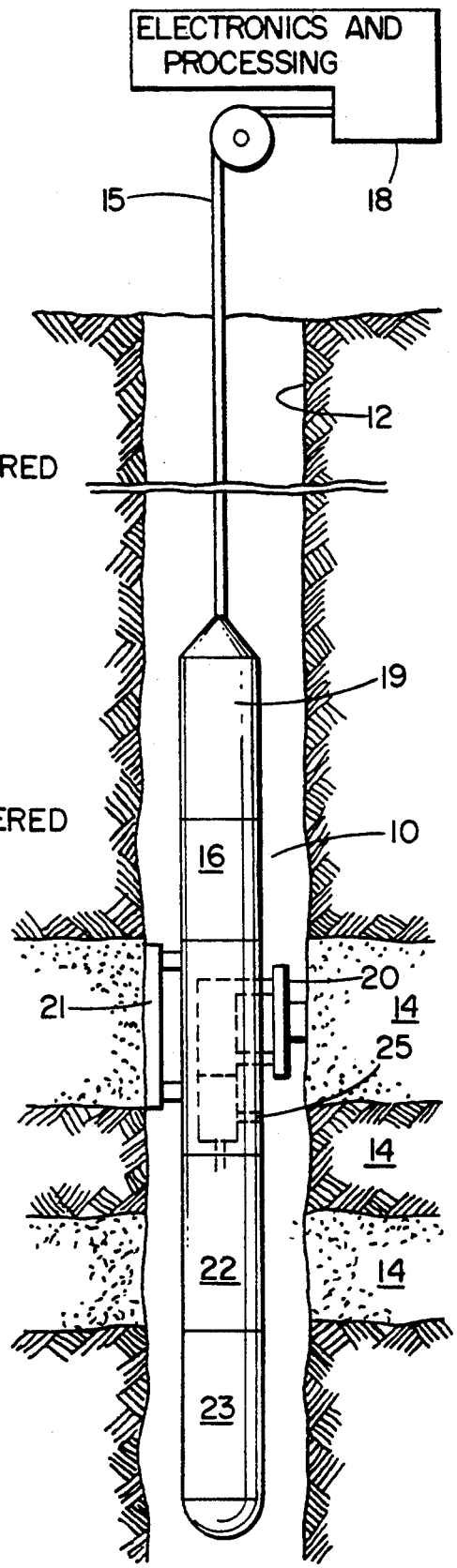
FIG. 2 is a schematic diagram of a borehole apparatus useful in conducting the methods of the invention.

The instant invention is particularly applicable to both production logging and to borehole investigative logging. For purposes of brevity, however, the description herein will be primarily directed to borehole investigative logging, and the terms "borehole" and "borehole tool" should be read throughout the specification and claims to encompass a, (cased) well and a tool used in a well, as well as in a borehole. Thus, a borehole tool 10 for testing earth formation and analyzing the composition of fluids from the formation 14 in accord with the invention is seen in FIG. 2. As illustrated, the tool 10 is suspended in the borehole 12 from the lower end of a typical multiconductor cable 15 that is spooled in the usual fashion on a suitable winch (not shown) on the formation surface. On the surface, the cable 15 is preferably electrically coupled to an electrical control system 18. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18.

Additional details of methods and apparatus for obtaining formation fluid samples may be had by reference to U.S. Pat. No. 3,859,851 to Urbanosky and U.S. Pat. No. 4,396,259 to Miller which are hereby incorporated by reference herein. It should be appreciated, however, that it is not intended that the invention be limited to any particular method or apparatus for obtaining the formation fluids. Likewise, details of an apparatus particularly suitable for the method of the invention hereinafter described, are set forth in previously incorporated U.S. Pat. No. 4,994,671. Again, however, it is not intended that the invention be limited thereby. It is noted, however, that preferably, the borehole too which is used to practice the preferred method of the invention includes a downhole processor (not shown) for carrying out arithmetic tasks as set forth below. Also, the borehole tool should preferably include an optical source for providing photons having energies defined by wavelengths of between 300 and 2500 nm and a means for determining the intensity of the light source at various wavelengths as well as the intensity of the light transmitted through the fluid sample at those wavelengths; i.e., spectral means for determining the absorption of the sample at a plurality of energy channels.

Figure 3:
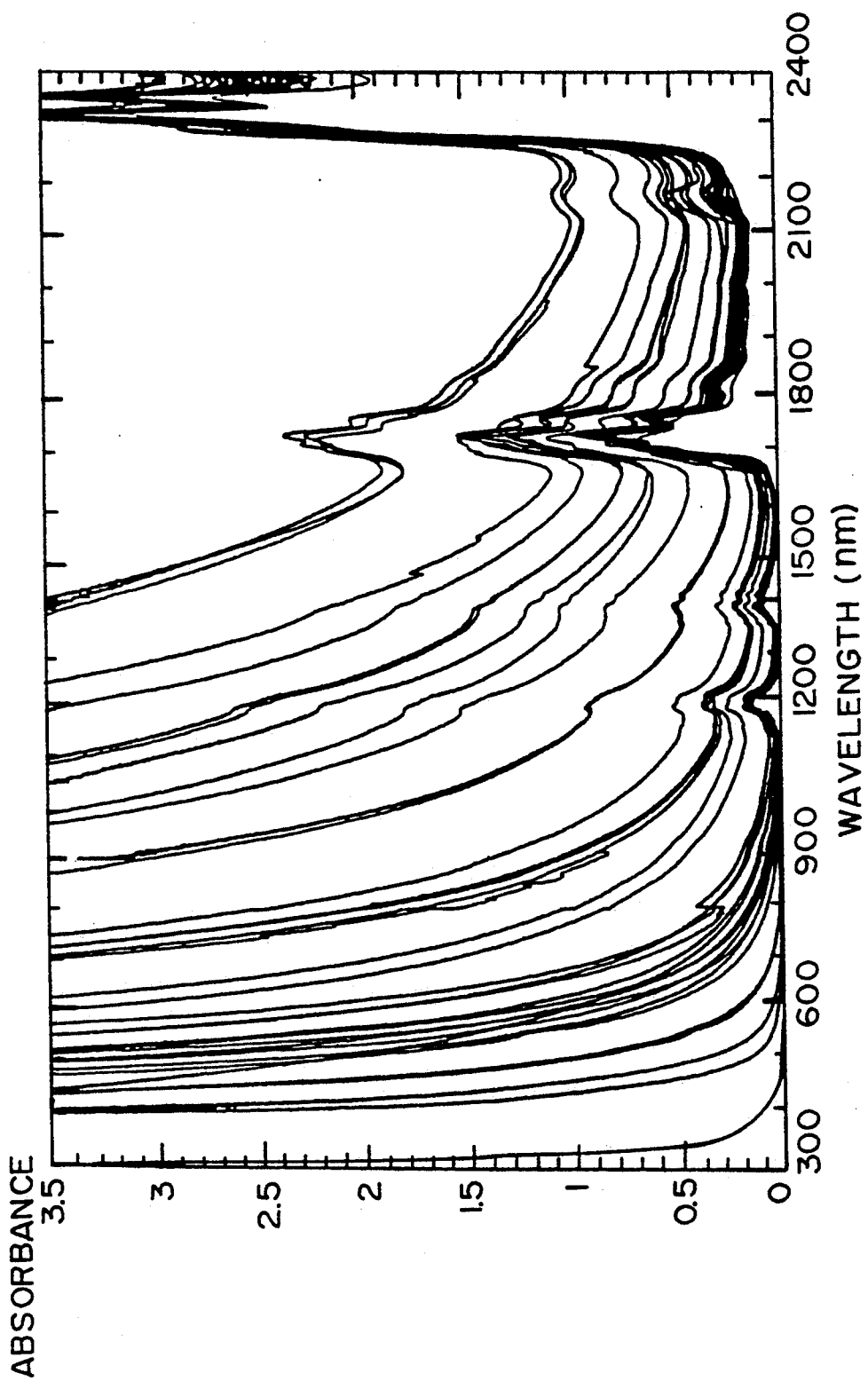
FIG. 3 is a graph showing the optical absorption curves or numerous crude oils as a function of wavelength.
Figure 4:
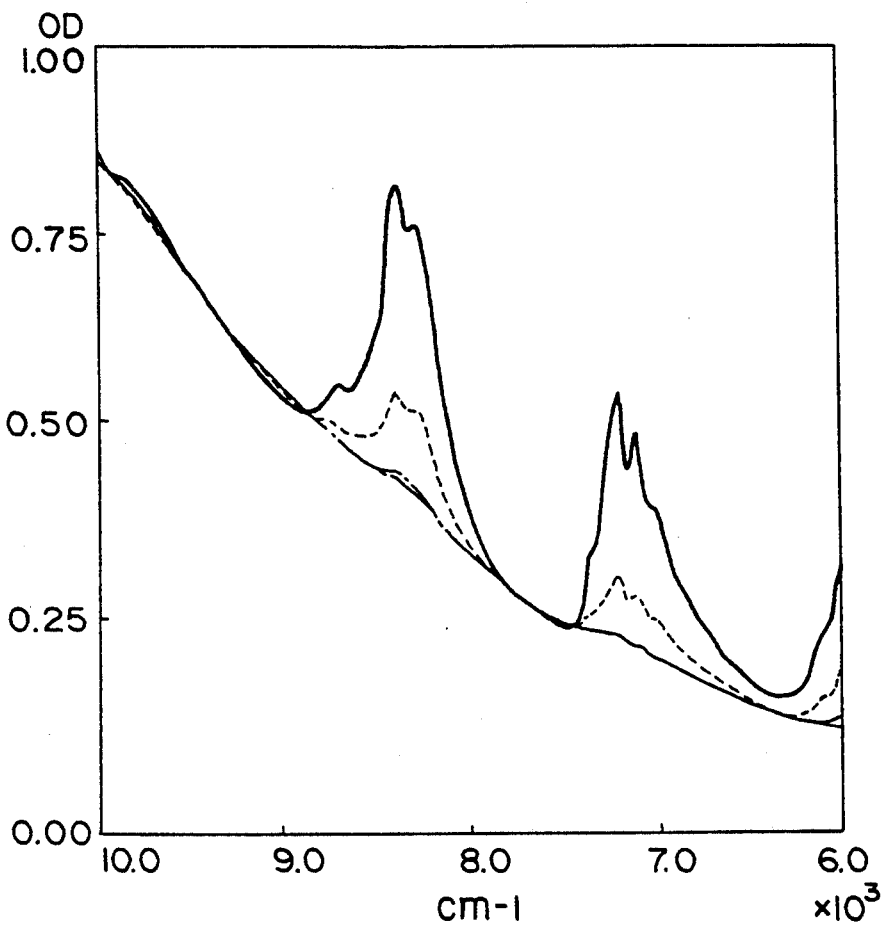
FIG. 4 is a graph showing scaled optical absorption curves of four different crude oils.
Figure 5:
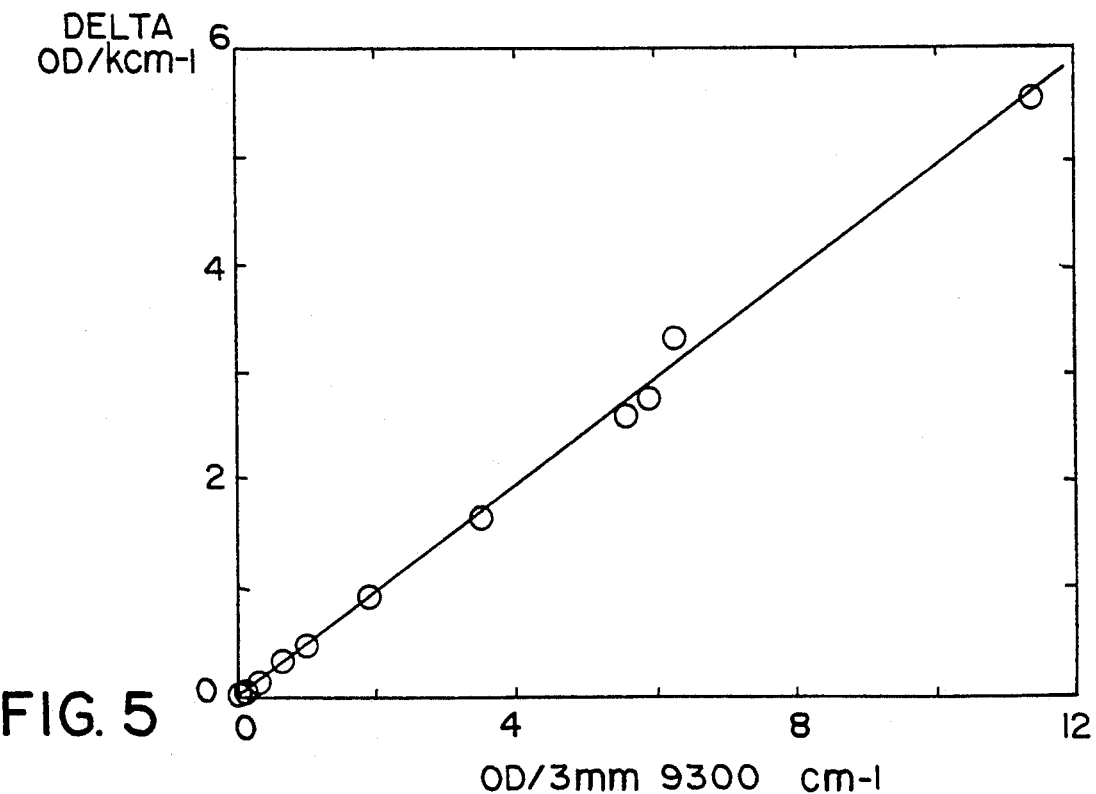
FIG. 5 is a graph where the slope versus optical density is plotted for the spectra of thirteen different crude oils.

The preferred method of the invention is best understood by making observations with reference to FIGS. 3-8. In particular in FIG. 3, the optical absorbances of approximately thirty crude oils are plotted as a function of wavelength in the near ultraviolet (300 to 400 nanometers), visible (400 to 700 nanometers) and near infrared (700 to 2500 nanometers) spectra. Of particular interest are the broad sloping absorption edges corresponding the electronic absorption as opposed to the peaks (1650-1750 nm, and 2240-2400 nm) which correspond to the vibrational overtones and combination bands of the vibrational absorption. Surprisingly, and as shown in FIG. 4, with respect to only four crude oils, the spectra of crude oils may be multiplicatively scaled such that their electronic absorption profiles substantially superimpose. The superimposition of FIG. 4 is obtained by normalizing the electronic absorption profiles of the four crude oils at exactly 9300 cm$^{-1}$. The fact that the spectra may be multiplicatively scaled is also seen with reference to FIG. 5, which shows the scaling for thirteen different crude oils where the slope of the optical density versus wavenumber is plotted against the optical density for the spectra of those crude oils. As seen in FIG. 5, a linear relationship exists at a given wavelength between the magnitude of the absorption (abscissa) and the magnitude of the slope in absorption versus wavenumber (ordinate) for all thirteen oils. The electronic absorption spectra of these oils scale linearly; i.e., the electronic absorption spectrum of one oil can be obtained by multiplying the spectrum of another oil by a constant. This constant is denoted below as (a) and is discussed in more detail below with reference to equation (1).

Figure 6:
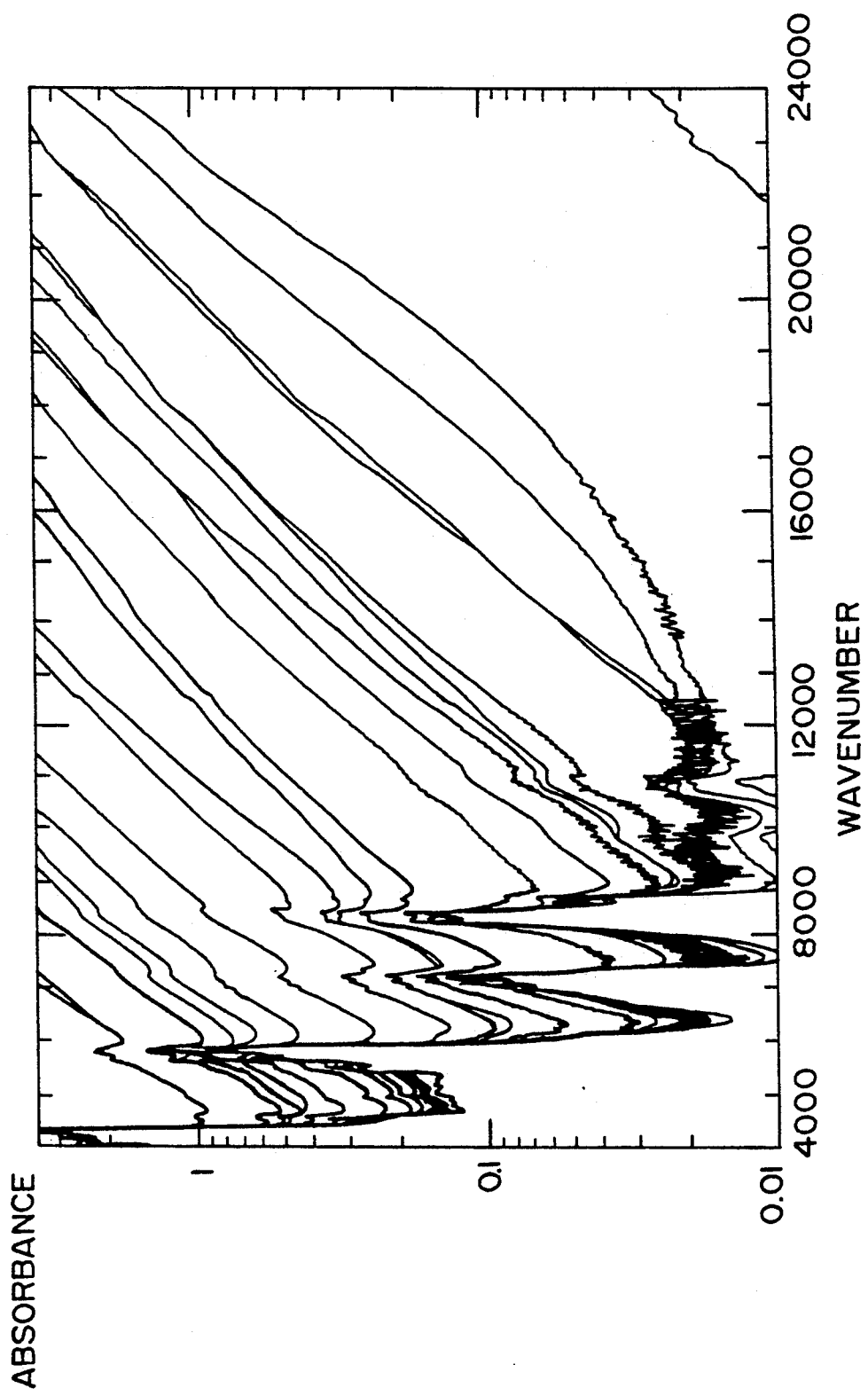
FIG. 6 is a graph plotting absorption on a logarithmic scale versus photon energy for many of the crude oils shown in FIG. 3.

Turning now to FIG. 6, the logarithm of the absorbance of many of the oils plotted in FIG. 3, is plotted against wavenumber (photon energy). As seen in FIG. 6, for the wavenumbers of interest (where electronic absorption dominates), the log of the absorbance scales linearly with the photon energies for the crude oils; i.e., an exponential relationship established. In addition, it is seen that the slopes of the curves of FIG. 6 are all quite similar and can be said to be equal to a constant. This "constant" is denoted below as (b) and is discussed in more detail below with reference to equation (1).

Based on the fact that the electronic absorption profiles of crude oils substantially superimpose when scaled in a multiplicative manner, and that the absorbance for these crude oils is an exponential function of wave number, it was determined that the equation $$OD = (a)e^{Eb} \quad (1)$$

provides an excellent fit to the absorption edges of the spectra, where OD is the optical density, E is the photon energy in wavenumbers (cm$^{-1}$), b is an exponential decay value (in cm) which is fairly constant for different spectra as described below, and (a) is an unknown multiplicative coefficient allowed to vary. Thus, it will be appreciated by those skilled in the art that a particular crude oil may be classified or defined simply according to its (a) value. Similarly, it will be appreciated by those skilled in the art, that different crude oils may be distinguished from each other by finding the optical densities of the oils and as a result thereof, finding the (a) values of the crude oils. As described below, the ability to easily distinguish between crude oils according to (a) values is useful in determining whether or not to take a fluid sample obtained by a borehole tool, where the fluid sample may be mud filtrate, formation fluid, or a combination thereof.

Figure 7:
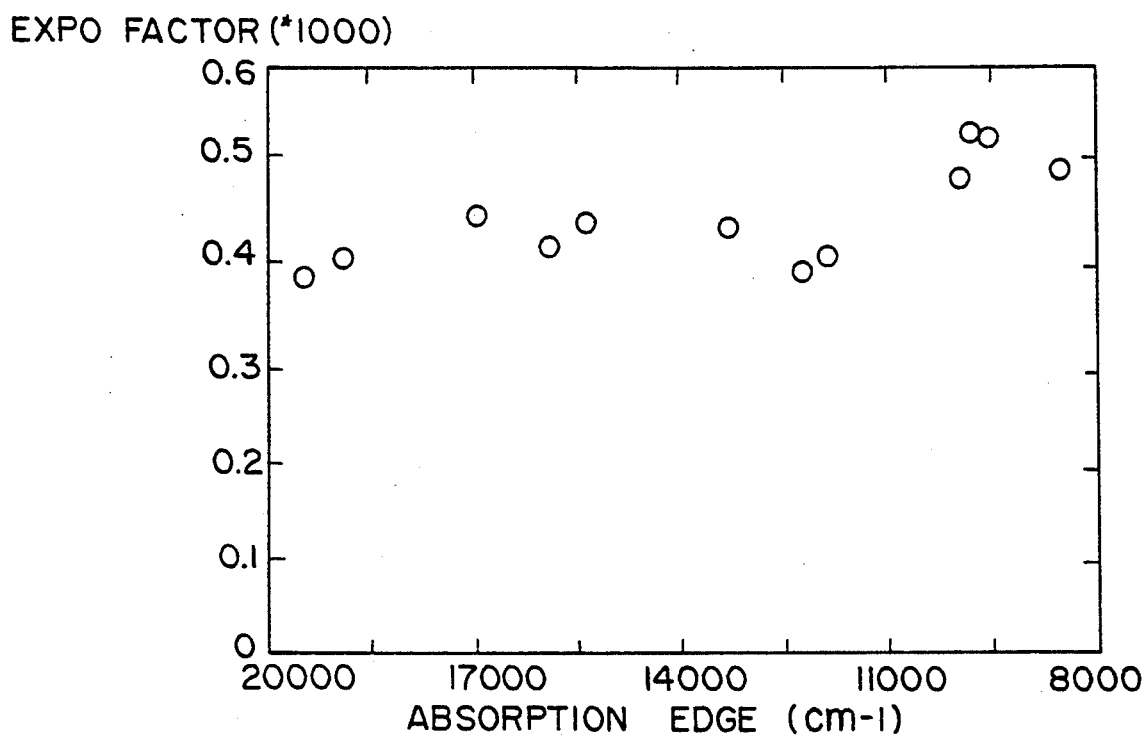
FIG. 7 is a graph of the exponential factor (b) as a function of the absorption edge for a plurality of crude oil spectra.

In order to determine the value for the exponential factor b, approximately twelve crude oil spectra were fit to equation (1), where both factors (a) and (b) were allowed to vary. A plot for the optimized values of the exponential factor b versus the absorption edge wavelengths of the various crude oils is seen in FIG. 7. As shown in FIG. 7, the exponential factor b varies from approximately 370 to 550, with an average of approximately 460 (standard deviation of about ten percent). Thus, while for absolute simplicity, b may be chosen to be a constant (e.g., 460) for a better determination of the factor (a), the (b) value can be permitted to vary as a function of wavelength. This information can be stored as a simple table relating the exponential factor (b) and the wavelength as determined according to experimental data.

Figure 8:
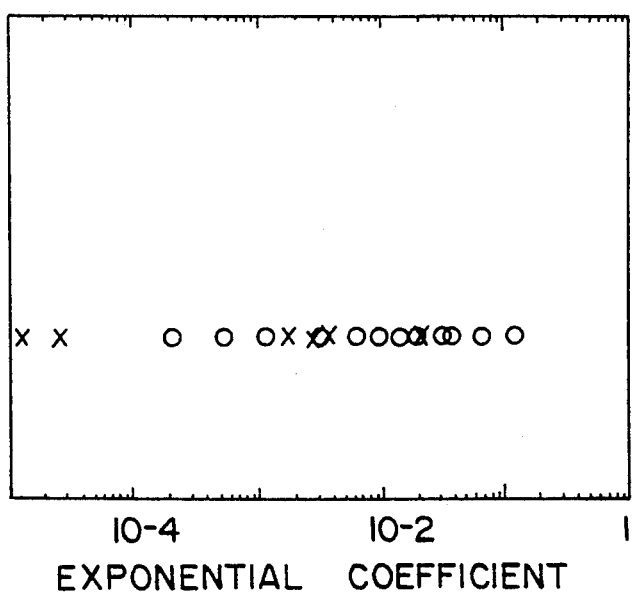
FIG. 8 is a chart showing the variation of the factor (a) for crude oils and oil base muds.

While the exponential factor (b) is shown to vary within a relatively small range, the value for variable (a) is seen in FIG. 8 to vary over a very wide range from $10^{-5}$ up to $10^{-1}$. While in some cases, the value for the (a) variable of an oil base mud filtrate (shown by x points) may be very similar to the value for a particular crude oil (shown by o points), in most cases, because of the wide range in (a) values, unless the crude oil in the mud filtrate exactly matches the crude oil in the formation, it will be possible to distinguish between the formation fluids and borehole filtrate.

In theory, based on equation (1) above, it is possible to characterize an oil by making a single optical density measurement of the oil sample. However, because the absorbance of many crude oils goes from an extremely small value to an extremely high value over a small wavelength range (e.g., three hundred nanometers) as seen in FIG. 2, and extremely small and high absorbance values are difficult, if not impossible, to accurately measure in a borehole tool, it is preferable to attempt to make density measurements at various wavelengths in at least the visible, and the near infrared spectra, and if desired in the ultraviolet (200-400 nm) spectrum. In this manner, it is likely that at least one measurement will be made at a wavelength where moderate absorbance is found for a particular crude oil. However, for the purpose of distinguishing among oils, in choosing channels, it is typically desirable to avoid the frequencies where vibrational absorption dominates in crude oils (e.g., 1150-1250, 1650-1800), as well as the frequency ranges where water has high absorption (i.e., 1350-1600, and 1850 and beyond) and will dominate the absorption. In a preferred embodiment of a tool incorporating the method of the invention, six channels are utilized with substantially equal spectral energy spacings. The channels are set at 476, 537, 647, 815, 1070, and 1300 nm. It will be appreciated by those skilled in the art, that several other channels may be included (1450, 1600, 1720, 1960 nm) but dominated by the water absorption, if water is present, and those channels are used for purposes outside of the scope of this invention.

Making optical measurements at more than one energy is also desirable in some situations where the optical density measurement includes scattering as well as absorption (e.g., where there may be two phase flow). In these situations, equation (1) above may be modified according to:

$$OD = (a)e^{Eb} + S \quad (2)$$

where S is a scattering term. Typically, the scattering is taken to be independent of wavelength. By taking optical density measurements at more than one energy (i.e., E is different for the measurements), a solution may be obtained for the two unknowns (a and S), as two equations are set forth.

Figure 9A:
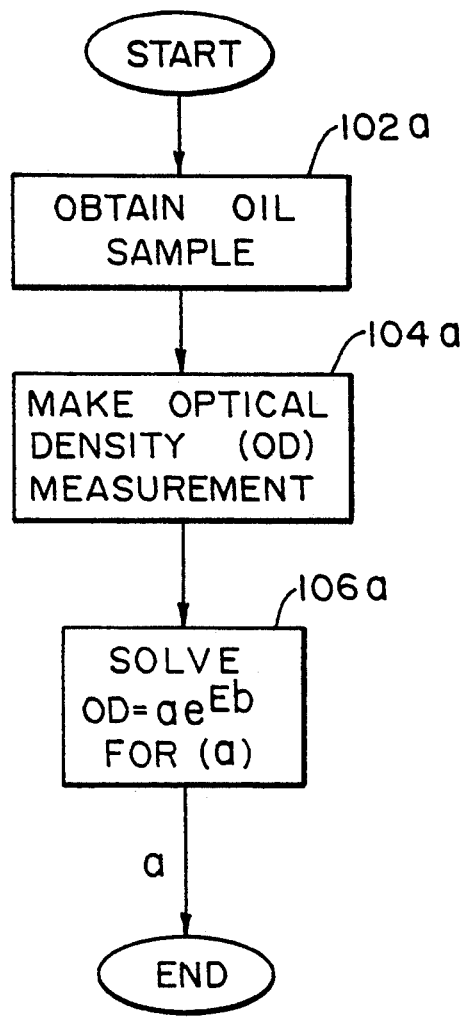
FIGS. 9a-9c are flow charts of the methods of the invention for classifying oils, for distinguishing among oils in a changing flow stream, and for distinguishing between mud filtrate and formation oil respectively.

As aforementioned, the apparatus for carrying out the method of the invention preferably includes a means for determining the optical density of a fluid sample at one or more wavelengths, and a processor for taking the absorption value and solving equation (1) for the variable (a). Based on the above discussion, it will be appreciated that methods for classifying and distinguishing among oil samples are accomplished by finding the (a) variable values for oil samples. In particular, and as set forth in FIG. 9a in flow chart format, a first method of the invention comprises obtaining an oil sample at step 102a. At step 104a, at least one optical density measurement (OD) is made of the oil sample with photons of at least one energy (and preferably a plurality of energies) in the visible and/or near infrared range (and the ultraviolet range if desired), where optical absorption of the photons is dominated by electronic absorption by the oil sample. At step 106a, each optical density measurement with its associated energy are input into equation (1) set forth above, the exponential value (b) is chosen as either a constant or according to the photon energy, and the equation is solved for the variable (a). The determination of variable (a) effectively classifies the oil sample, and is shown as the output of the method in FIG. 9a.

Figure 9B:
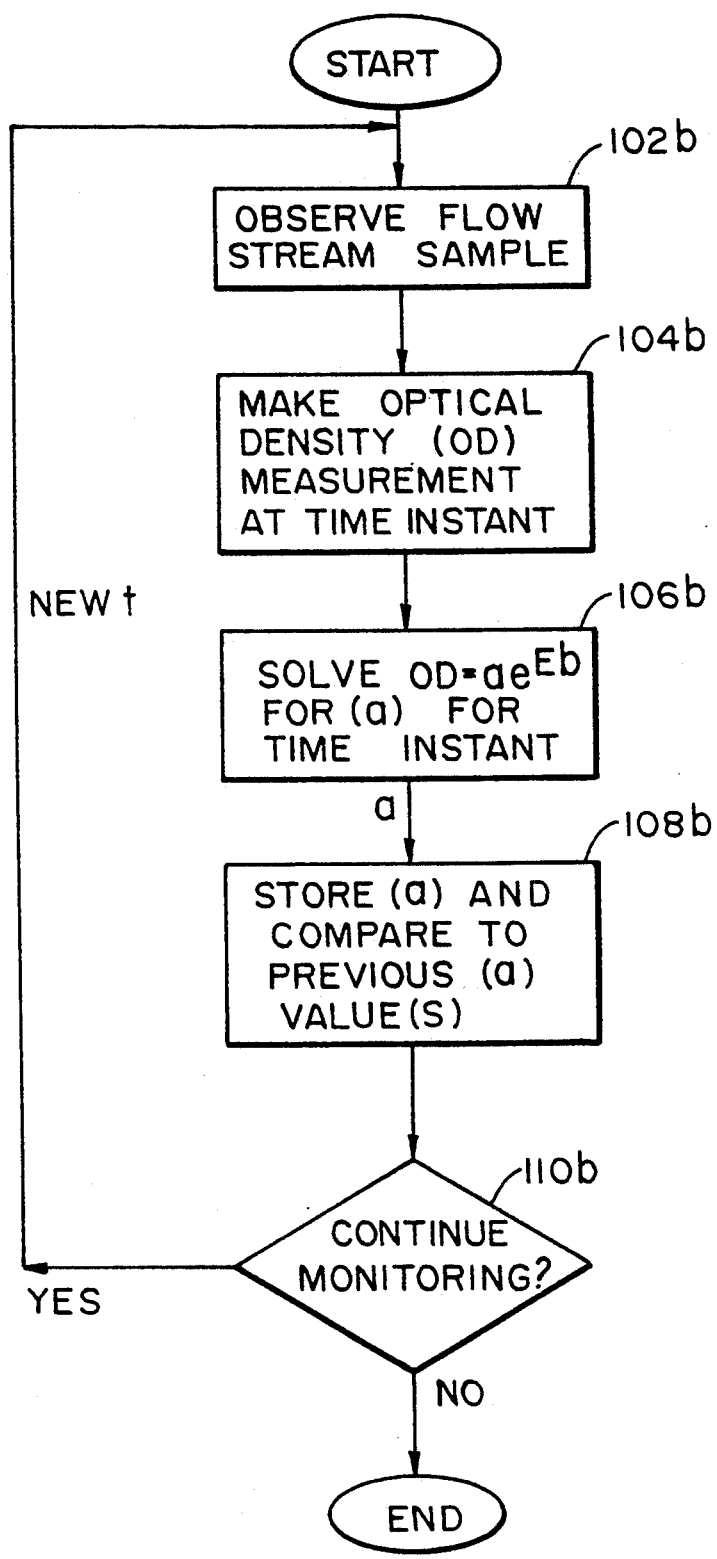

Turning to FIG. 9b, a similar method is shown, except that instead of a single oil sample, a fluid flow stream is being monitored for a change of oils over time, where the oils constitute a portion of the fluid flow stream. At step 102b, the flow stream is sent through an observation module. At step 104b, at least one optical density measurement (OD) is made at a particular time of the flow stream with photons of at least one energy in the visible and/or near infrared range, where optical absorption of the photons is dominated by electronic absorption by the oil sample. At step 106b, each optical density measurement with its associated energy are input into equation (1) set forth above, the exponential value (b) is chosen as either a constant or according to the photon energy, and the equation is solved for the variable (a). The determination of variable (a) effectively classifies the oil found in the fluid flow stream sample at the particular time. Thus, at step 108b, the value of (a) is stored and compared against a previous value or values (a) for previous samples (if available) to determine whether the oil type in the flow stream is changing. If monitoring is to continue, as indicated at 110b, steps 104b, 106b, and 108b are repeated to determine the (a) value for the next flow stream sample. The process repeats until the flow stream stops or until comparison is no longer desired.

Figure 9C:
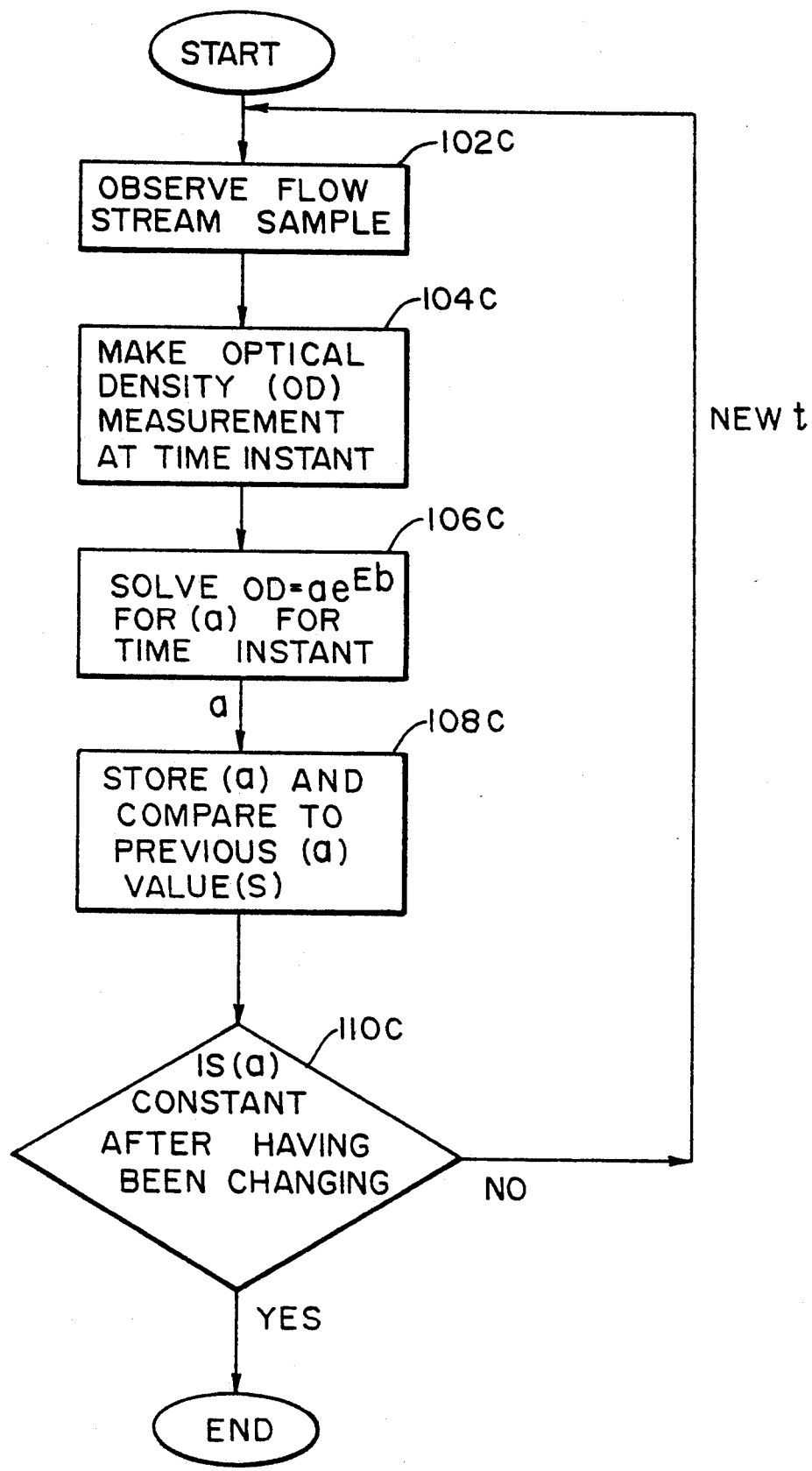

A method for monitoring a fluid flow stream in a borehole tool is seen in FIG. 9c. The method of FIG. 9c is very similar to that of FIG. 9b. At step 102c, the flow stream is sent through an observation module in the borehole tool. At step 104c, at least one optical density measurement (OD) is made at a particular time of the flow stream with photons of at least one energy in the visible and/or near infrared range, where optical absorption of the photons is dominated by electronic absorption by the oil sample. At step 106c, each optical density measurement with its associated energy are input into equation (1) set forth above, the exponential value (b) is chosen as either a constant or according to the photon energy, and the equation is solved for the variable (a). The determination of variable (a) effectively classifies the oil found in the fluid flow stream sample at the particular time. Thus, at step 108c, the value of (a) is stored and compared against a previous value or values for previous samples (if available) to determine whether the oil type in the flow stream is changing; i.e., a change from mud filtrate to formation oil. More particularly, and in accordance with a preferred aspect of the invention, the value of (a) is monitored over time. Typically, the value of (a) will remain constant over a first time period when mud filtrate is being obtained in the flow stream, will change over a second time period when mud filtrate and formation oil are being received together in the flow stream, and will remain relatively constant over a third period of time when only formation oil is being received in the flow stream. Since it is typically desired to obtain formation oil samples as opposed to mud filtrate or mixed samples, it is only in the third period of time when the (a) value has steadied after a period of changing (a) values that samples should be taken. Thus, the determination of whether to continue monitoring at step 110c is made based on whether the (a) value has steadied after a period of changing (a) values. If monitoring is to continue, i.e., either the (a) value has not started changing or is still changing, steps 104c, 106c, and 108c are repeated to determine the (a) value for the next flow stream sample. The process repeats until comparison is no longer desired.

There have been described and illustrated herein methods for classifying and distinguishing among oils. While particular embodiments of the invention have been described and illustrated, it is not intended that the invention be limited thereby, as it is intended that the invention be as broad in scope as the art will allow. Thus, while a particular equation utilizing the optical density (OD), an exponential factor (b), and the photon energy E in wavenumbers as inputs, in order to find an unknown coefficient (a), it will be appreciated that various changes could be made to the equation without deviating from the scope of the teaching. In particular, while the energy in wavenumbers is provided as an input, it will be appreciated that the wavelength of a photon is the inverse of the wavenumber (1/wavenumber). Hence, instead of utilizing the wavenumber, the wavelength associated with the wavenumber could be utilized. However, for purposes herein, the resulting equation is exactly equivalent to the stated equation. Likewise, it will be appreciated that the optical absorption may be expressed as a transmittance value and substituted in the stated equation in lieu thereof. Again, for purposes herein, the resulting equation will be equivalent. Further, it will be appreciated that equations (1) or (2) can be modified by increasing the number of variables (e.g., an $a_2$, $a_2$ . . . ), and/or by expanding the argument of the exponential. Regardless, the term $ae^{Eb}$ will be a dominant term in the solution, and it is intended that the invention encompass these changes which are more changes in form than in substance. Therefore, it will be apparent to those skilled in the art that other changes and modifications may be made to the invention as described in the specification without departing from the spirit and scope of the invention as so claimed.

I claim:

1. A method for classifying an oil sample, comprising:
    a) making an optical density measurement (OD) of said oil sample by detecting photons of at least one energy defined by wavenumbers (E) whose wavelenqths are between 200 and 2500 nm, wherein said at least one energy is chosen such that the optical absorption of said photons at said at least one energy is dominated by electronic absorption by said oil sample;
    b) using said optical density measurement OD, solving an equation relating said optical density measurement OD to a dominant term $ae^{Eb}$ for an unknown (a), where (a) classifies the oil type, (E) is the wavenumber which is the inverse of the wavelength, and where (b) is an exponential decay value for said oil sample.

2. A method according to claim 1, wherein:
b is a value between $0.37 \times 10^{-4}$ cm and $0.55 \times 10^{-4}$ cm chosen according to E.

3. A method according to claim 1, wherein:
b is a constant regardless of E value.

4. A method according to claim 1, wherein:
said equation relating said optical density measurement OD to a dominant term $ae^{Eb}$ is substantially of the form $$OD = ae^{Eb} + S$$

where S is a term relating to scattering of photons, and
optical density measurements are made for photons of at least two different energies.

5. A method according to claim 4, wherein:
said at least two different energies include energies defined by wavelengths between 200 and 2500 nm.

6. A method according to claim 4, wherein:
S is taken as zero.

7. A method for monitoring a fluid flow stream for a change over time of oils which constitute of a portion of said fluid flow stream, said method comprising:
a) making optical density measurements (OD) of said fluid flow stream over time by detecting photons having an energy with wavelengths in at least the visible or near infrared spectrum;
b) determining a change in an oil classification variable (a) over time by solving for said oil classification variable (a) in an equation relating said optical density measurements OD to a dominant term $ae^{Eb}$, where E is the inverse of the wavelength or a wavenumber corresponding to said wavelength, and b is an exponential decay value for oils in said fluid flow stream.

8. A method according to claim 7, wherein:
b is a value between $0.37 \times 10^{-4}$ cm and $0.55 \times 10^{-4}$ cm chosen according to E.

9. A method according to claim 7, wherein:
b is a constant regardless of E value.

10. A method according to claim 7, wherein:
said equation relating said optical density measurements OD to a dominant term $ae^{Eb}$ is substantially of the form $$OD = ae^{Eb} + S$$

where S is a term relating to scattering of photons, and
said optical density measurements are made for photons having at least two different energies defined by wavelengths between 200 and 2500 nm.

11. A method according to claim 10, wherein:
S is taken as zero.

12. An in situ method for monitoring fluids obtained over time by a borehole tool in a borehole in order to determine when said borehole tool is obtaining primarily formation fluids as opposed to an oil based mud filtrate, said method comprising:
a) making a plurality of optical density measurements (OD) with said borehole tool in said borehole of the obtained fluid over time by detecting photons of energy with wavelengths located in the visible or near infrared spectra;
b) repeatedly solving an equation relating said optical density measurements OD to a dominant term $ae^{Eb}$, for (a), with said plurality of optical density measurements (OD) and said energy as inputs to said equation, where (a) is an oil classification variable, E is the inverse of the wavelength or a wavenumber corresponding to said wavelength, and where b is an exponential decay value for oils in the monitored fluids; and
c) monitoring (a) for changes in value.

13. An in situ method according to claim 12, wherein:
said step of monitoring comprises monitoring (a) for changes in value over a first time period and for substantial stability in value over a second time period after said first time period, whereby a determination is made that primarily formation fluids are being obtained in at least said second time period.

14. An in situ method according to claim 12, wherein:
b is a value between $0.37 \times 10^{-4}$ cm and $0.55 \times 10^{-4}$ cm chosen according to E.

15. A method according to claim 12, wherein:
b is a constant regardless of E value.

16. A method according to claim 12, wherein:
said equation relating said optical density measurements OD to a dominant term $ae^{Eb}$ is substantially of the form $$OD = ae^{Eb} + S$$

where S is a term relating to scattering of photons, and
said optical density measurements are made for photons having at least two different energies defined by wavelengths between 200 and 2500 nm.

17. A method according to claim 13, wherein:
b is a value between $0.37 \times 10^{-4}$ cm and $0.55 \times 10^{-4}$ cm chosen according to E.

18. A method according to claim 13, wherein:
b is a constant regardless of E value.

19. A method according to claim 13, wherein:
said equation relating said optical density measurements OD to a dominant term $ae^{Eb}$ is substantially of the form $$Od = ae^{Eb} + S$$

where S is a term relating to scattering of photons, and
said optical density measurements are made for photons having at least two different energies defined by wavelengths between 200 and 2500 nm.

20. A method according to claim 19, wherein:
S is taken as zero.

* * * * *